United States Patent
Rizk

(10) Patent No.: US 11,504,358 B2
(45) Date of Patent: *Nov. 22, 2022

(54) EXTENDED RELEASE METHAZOLAMIDE FORMULATION

(71) Applicant: Effcon Laboratories, Inc., Marietta, GA (US)

(72) Inventor: Nabil Rizk, Montville, NJ (US)

(73) Assignee: Effcon Laboratories, Inc., Marietta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/394,059

(22) Filed: Aug. 4, 2021

(65) Prior Publication Data

US 2022/0160684 A1    May 26, 2022

Related U.S. Application Data

(63) Continuation of application No. 16/683,930, filed on Nov. 14, 2019, now Pat. No. 11,103,485, which is a continuation of application No. 15/972,943, filed on May 7, 2018, now Pat. No. 10,493,063, which is a continuation of application No. 15/621,298, filed on Jun. 13, 2017, now Pat. No. 9,980,946.

(60) Provisional application No. 62/450,233, filed on Jan. 25, 2017.

(51) Int. Cl.
*A61K 31/43* (2006.01)
*A61K 31/433* (2006.01)
*A61K 9/20* (2006.01)

(52) U.S. Cl.
CPC .......... *A61K 31/433* (2013.01); *A61K 9/2054* (2013.01); *A61K 2300/00* (2013.01)

(58) Field of Classification Search
CPC ........ A61K 31/43; A61K 9/2054; A61K 9/16; A61K 9/14; A61K 9/141; A61K 9/2004; A61K 9/205; A61K 9/2059
See application file for complete search history.

(56) References Cited

U.S. PATENT DOCUMENTS

| | | |
|---|---|---|
| 4,259,314 A | 3/1981 | Lowey |
| 4,357,469 A | 11/1982 | Schor |
| 4,369,172 A | 1/1983 | Schor et al. |
| 4,389,393 A | 6/1983 | Schoar et al. |
| 4,540,566 A | 12/1985 | Davis et al. |
| 4,617,186 A | 10/1986 | Schäfer et al. |
| 4,663,322 A | 5/1987 | Beyer, Jr. |
| 4,734,285 A | 3/1988 | Alderman |
| 4,775,535 A | 10/1988 | Lowey |
| 4,795,327 A | 1/1989 | Gaylord et al. |
| 4,851,232 A | 7/1989 | Urquhart et al. |
| 4,855,143 A | 8/1989 | Lowey |
| 4,871,548 A | 10/1989 | Edgren et al. |
| 4,946,685 A | 8/1990 | Edgren et al. |
| 4,983,398 A | 1/1991 | Gaylord et al. |
| 5,009,897 A | 4/1991 | Brinker et al. |
| 5,104,887 A | 4/1992 | Schoenwald et al. |
| 5,126,145 A | 6/1992 | Evenstad et al. |
| 5,157,044 A | 10/1992 | Schoenwald et al. |
| 5,225,424 A | 7/1993 | Schoenwald et al. |
| 5,232,705 A | 8/1993 | Wong et al. |
| 5,283,065 A | 2/1994 | Doyon et al. |
| 5,348,746 A | 9/1994 | Dong et al. |
| 5,366,738 A | 11/1994 | Rork et al. |
| 5,393,765 A | 2/1995 | Infeld et al. |
| 5,419,918 A | 5/1995 | Lundberg |
| 5,422,116 A | 6/1995 | Yen et al. |
| 5,458,887 A | 10/1995 | Chen et al. |
| 5,585,243 A | 12/1996 | Aster et al. |
| 5,776,489 A | 7/1998 | Preston et al. |
| 6,214,381 B1 * | 4/2001 | Burklow .............. A61K 9/2054 514/777 |
| 9,980,946 B1 * | 5/2018 | Rizk ..................... A61K 9/2054 |
| 10,493,063 B2 * | 12/2019 | Rizk ..................... A61K 31/433 |
| 11,103,485 B2 * | 8/2021 | Rizk ..................... A61K 31/433 |
| 2004/0247679 A1 | 12/2004 | Lin et al. |
| 2009/0028938 A1 | 1/2009 | Berndl et al. |

FOREIGN PATENT DOCUMENTS

| | | |
|---|---|---|
| EP | 0201057 B1 | 12/1992 |
| EP | 0501678 B1 | 5/1996 |
| JP | 0565227 A | 3/1993 |

* cited by examiner

*Primary Examiner* — Micah Paul Young
(74) *Attorney, Agent, or Firm* — Eversheds Sutherland (US) LLP

(57) ABSTRACT

A once-a-day controlled release oral dosage form of methazolamide is provided. The dosage form comprises a therapeutically effective amount of methazolamide and a high molecular weight binder. The dosage is configured for once-daily administration to a subject in need thereof, and releases methazolamide over a period of about twenty-four hours.

20 Claims, 1 Drawing Sheet

EXTENDED RELEASE METHAZOLAMIDE FORMULATION

CROSS REFERENCES TO RELATED APPLICATIONS

This application is a continuation of U.S. application Ser. No. 16/683,930, filed Nov. 14, 2019, which is a continuation of Ser. No. 15/972,943, now U.S. Pat. No. 10,493,063, issued Dec. 3, 2019, which is a continuation of U.S. application Ser. No. 15/621,298, now U.S. Pat. No. 9,980,946, issued May 29, 2018, which claims priority to U.S. Provisional Application No. 62/450,233, filed Jan. 25, 2017, the entire contents of which is incorporated by reference herewith.

FIELD OF INVENTION

The present disclosure generally relates to an extended release formulation of methazolamide. More specifically, it relates to an oral dosage form of methazolamide which provides a release profile suitable for once daily dosing while exhibiting good bioavailability.

BACKGROUND OF THE INVENTION

Ocular conditions characterized by elevated intraocular pressure, such as chronic open-angle glaucoma or secondary glaucoma, have been successfully treated by administration of methazolamide, and analogs, derivatives, and prodrugs thereof. Methazolamide is a carbonic anhydrase inhibitor that slows the formation of excess fluids behind the cornea by inhibiting a chemical reaction at the ciliary body.

Methazolamide is commercially available as an oral dose in 25 and 50 mg immediate release tablets, and is typically taken by a patient two to three times daily (50-150 mg/day). While effective, the high dosing frequency a patient must follow in order to attain effective therapy using the commercially available immediate release tablets reduces patient compliance because patients often miss doses as a result of patient forgetfulness or the inconvenience of having to take multiple doses throughout the day. Therefore, it is desirable to have an extended release methazolamide formulation that provides a longer period of pharmacological action after administration than is ordinarily obtained after administration of immediate-release dosage forms.

Many techniques have been used to provide controlled and extended-release pharmaceutical dosage forms in order to maintain therapeutic serum levels of medicaments. However, in the case of relatively water insoluble drugs such as methazolamide, developing a sustained release formulation generally requires considerable experimentation because it is often not possible to readily predict whether a particular extended release formulation will yield the desired sustained release profile while also maintaining suitable handling properties such as sufficient tablet hardness and appropriate friability.

Owing to the fact that water insoluble drugs tend to yield inconsistent drug release profiles, the task of preparing controlled release formulations of methazolamide has proven difficult. There is no commercially available extended release methazolamide formulation on the market.

U.S. Pat. No. 6,214,381 describes an extended-release methazolamide formulation that releases methazolamide over a period of 12 hours or less. However, this formulation is inadequate for once daily dosing because the methazolamide release profile is not optimal and does not provide sufficient coverage over a 24 hour period. Further, this formulation cannot be readily used in a 24 hour extended-release methazolamide formulation because attempts to extend the drug release profile from 12 hours to 24 hours using this formulation results in a composition which has inadequate handing properties (e.g. compressibility and friability issues), thereby precluding the composition's use as an orally administrable once-a-day dose.

Therefore, what are needed are extended release formulations of methazolamide that can deliver methazolamide over 24 hours with a suitable drug release profile when given to a subject, thus allowing once daily oral administration.

SUMMARY OF THE INVENTION

This disclosure generally provides extended release formulations of methazolamide that can deliver methazolamide over 24 hours. The formulations exhibit sustained-release properties adequate to provide therapeutic effectiveness when administered orally not more than once daily to a subject in need thereof.

According to one aspect of the present disclosure, there is provided a once-a-day controlled release oral dosage form including a drug selected from methazolamide, a methazolamide analog, a methazolamide derivative, a methazolamide prodrug, or a combination thereof; and a high molecular weight binder, wherein the dosage form provides an in vitro release of from about 50% to about 80% by weight of the drug at 12 hours when measured by the USP Paddle Method at 100 rpm in acetate buffer (pH=4.5), and wherein the dosage form provides an in vitro release of about 90% or greater by weight of the drug at 24 hours when measured by the USP Paddle Method at 100 rpm in acetate buffer (pH=4.5).

According to another aspect of the present disclosure, there is provided a method for treating an ocular condition characterized by elevated intraocular pressure including administering to a patient in need thereof a once-a-day controlled release oral dosage form of methazolamide.

BRIEF DESCRIPTION OF THE DRAWINGS

Referring now to the drawings, which are meant to be exemplary and not limiting, and wherein like elements are numbered alike. The detailed description is set forth with reference to the accompanying drawings illustrating examples of the disclosure, in which use of the same reference numerals indicates similar or identical items. Certain embodiments of the present disclosure may include elements, components, and/or configurations other than those illustrated in the drawings, and some of the elements, components, and/or configurations illustrated in the drawings may not be present in certain embodiments.

DETAILED DESCRIPTION OF THE INVENTION

Figure 1:
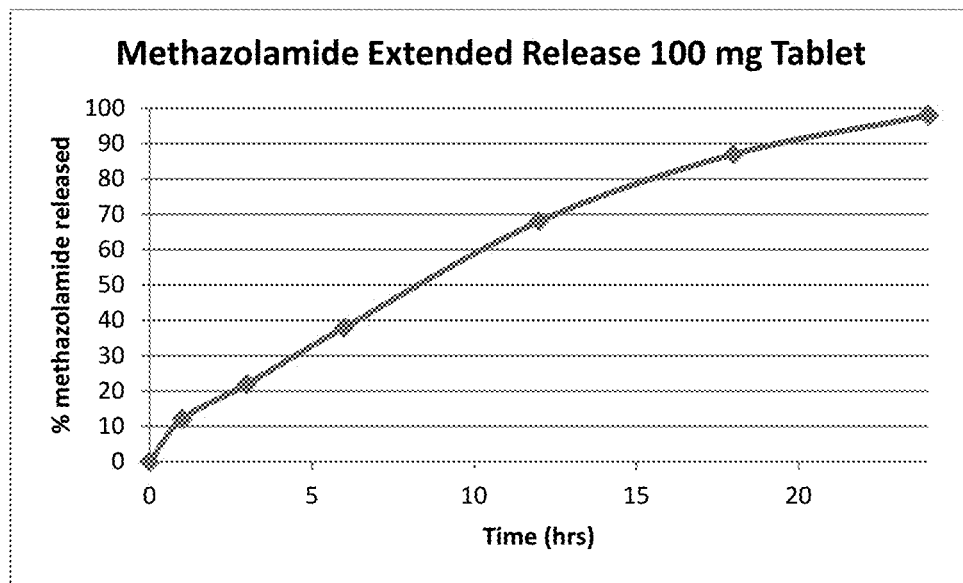
FIG. 1 shows a drug release profile of one embodiment of a pharmaceutical composition.
Figure 2:
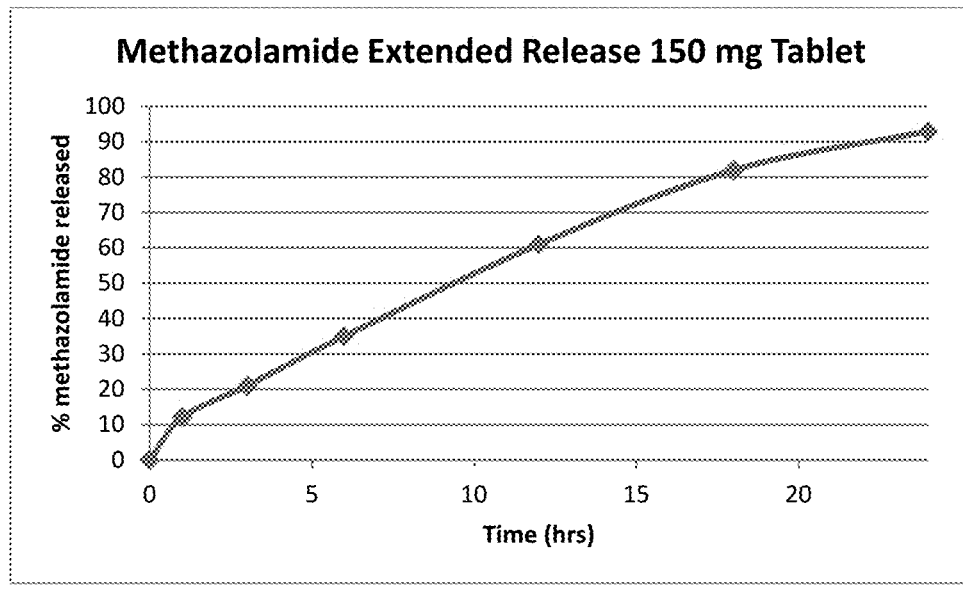
FIG. 2 shows a drug release profile of one embodiment of a pharmaceutical composition.

After rigorous investigation, the inventors surprisingly found it possible to produce an extended release oral dose formulation of methazolamide for once daily administration that releases methazolamide over a period of twenty-four hours. More particularly, the inventors surprisingly discovered that a composition formed from a unique range of methazolamide particle sizes not present in prior formulations, in combination with an increase in excipient viscosity and/or excipient percentage in the composition relative to prior formulations, resulted in a methazolamide composition that releases methazolamide over a twenty-four hour period, thereby providing a composition suitable for use in a once-a-day dosing regimen.

It is understood that aspects and embodiments of the invention described herein include "consisting" and/or "consisting essentially of" aspects and embodiments.

As used herein, "about" refers to within 10% of a stated value. For example, about 50 encompasses 45 to 55, inclusive. When the term "about" modifies a numerical range, the term applies to both ends of the range (e.g. about 5 to 10 means about 5 to about 10).

Throughout this disclosure, various aspects of the invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, "subject" or "patient" refers to an animal, a non-human mammal or a human. As used herein, "animals" include a pet, a farm animal, an economic animal, a sport animal and an experimental animal, such as a cat, a dog, a horse, a cow, an ox, a pig, a donkey, a sheep, a lamb, a goat, a mouse, a rabbit, a chicken, a duck, a goose, a primate, including a monkey and a chimpanzee.

Formulations

The present disclosure provides an extended release oral dose of methazolamide that exhibits sustained-release properties adequate to provide therapeutic effectiveness when administered orally not more than once daily to a subject in need thereof. The extended release doses are formulated to provide a sustained rate of methazolamide drug release in vivo over twenty-four hours. The pharmaceutical compositions generally comprise methazolamide and a high molecular weight binder. The compositions can also include fillers, lubricants, and/or flow agents. Tablets are the preferred oral dosage form for the methazolamide compositions of the present disclosure; however, this disclosure contemplates that the compositions may also be formulated as hard gel capsules, soft gel capsules, and the like.

The active ingredient in the pharmaceutical formulations described herein is methazolamide, a methazolamide analog, a methazolamide prodrug, and/or a methazolamide derivative. Methazolamide, a sulfonamide derivative, is a white crystalline powder, weakly acidic, and slightly soluble in water, alcohol and acetone. The chemical name for methazolamide is: N-[5-(aminosulfonyl)-3-methyl-1,3,4-thiadiazol-2(3H)-ylidene]acetamide. As used herein, methazolamide, methazolamide analogs, methazolamide prodrugs, and methazolamide derivatives also include salts thereof. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. The active ingredient can be obtained from any suitable source.

Exemplary methazolamide analogs include acetazolamide, hydroxymethazolamide, 6-[β-glucopyranosyl)oxyethoxy]-2-benzothiazolesulfonamide, N-[5-(aminosulfonyl)-3-methyl-1,3,4-thiadiazol-2(3H)-ylidene]-2-[glycolylhydroxy]acetamide, N-[5-(aminosulfonyl)-3-methyl-1,3,4-thiadiazol-2(3H)-ylidene]-2-hydroxypropanamide, N-[5-(aminosulfonyl)-3-methyl-1,3,4-thiadiazol-2-(3H)-ylidene]-2-D-glucuronamide, 2-benzyloxycarbonylimino-3-methyl-delta$^4$-1,3,4-thiadiazoline-5-sulfonamide, 2-[4-pyridylmethyloxy-carbony]imino-3-methyl-delta$^4$-1,3,4-thiadiazoline-5-sulfonamide, 2-[4-hydroxymethylbenzyloxycarbonyl]imino-3-methyl-delta$^4$-1,3,4-thiadiazoline-5 sulfonamide], 2-[4-hydroxymethylphenylacetyl]-imino-3-methyl-delta$^4$-1,3,4-thiadiazoline-5-sulfonamide, 2-ethoxycarbonylimino-3-methyl-delta$^4$-1,3,4-thiadiazoline-5-sulfonamide, 2-[4-pyridylmethyloxycarbony]imino-3-methyl-delta$^4$-1,3,4-thiadiazoline-5-sulfonamide, 2-[4-hydroxymethylbenzyloxycarbonyl]imino-3-methyl-delta$^4$-1,3,4-thiadiazoline-5-sulfonamide, and 2-[4-hydroxymethylphenylacetyl]imino-3-methyl-delta$_4$-1,3,4-thiadiazoline-5-sulfonamide. Additional methazolamide analogs can be found, for example, in U.S. Pat. Nos. 5,157,044 and 5,104,887, the contents of which are incorporated herein in their entirety.

Exemplary methazolamide prodrugs can include hydroxymethazolamides of the formula:

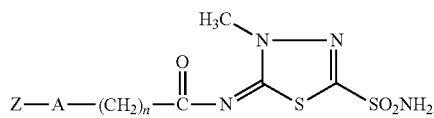

wherein "Z" represents a water soluble carrier (e.g. monosaccharides such as D- and L-glucose, 6-carboxylic acid derivatives of monosaccharides such as D- and L-glucuronic acid, and D- and L-gluconic acid, and the like) and "A" is a moiety which is attached to the carbonic anhydrase inhibitor which allows it to still retain carbonic anhydrase inhibitory activity, but also form an enzymatically cleavable bond between A and Z (e.g. a $C_1$ to $C_5$ alkyl such as a hydroxyethoxy, hydroxy, hydroxyacetamido, and amino). Additional details regarding exemplary methazolamide prodrugs can be found, for example, in U.S. Pat. No. 5,095,026, the contents of which are incorporated herein in their entirety.

Exemplary methazolamide derivatives can include N-[5-(aminosulfonyl)-3-methyl-1,3,4-thiadiazol-2(3H)-ylidene]-2-acetyloxyacetamide. Additional details regarding exemplary methazolamide derivatives can be found, for example, in U.S. Pat. No. 5,225,424, the contents of which are incorporated herein in their entirety.

The pharmaceutical compositions described herein can comprise about 50 mg to 500 mg of methazolamide per dose. In preferred embodiments, the pharmaceutical compositions comprise about 50 mg to 300 mg of methazolamide per dose. Thus, in preferred embodiments, a pharmaceutical composition can comprise, for example, about 50, 75, 100, 125, 150, 175, 200, 225, 250, 275, or 300 mg of methazolamide per dose. The exact amount of methazolamide is preferably selected such that the pharmaceutical compositions provide a single, once-a-day, therapeutically effective dose of methazolamide. By once-a-day dose of methazolamide, it is meant that the pharmaceutical composition releases methazolamide over an approximately 24 hour period such that an individual need only take a single dose per day.

The methazolamide particles in the pharmaceutical compositions can have any suitable size distribution. In some embodiments, the methazolamide particles have the following size distribution: a D(v, 0.5) of about 1 µm to 300 µm. In some embodiments, the methazolamide particles have the following size distribution: a D(v, 0.1) of about 1 µm to 100 µm, and a D(v, 0.9) of about 200 µm to 300 µm. In some embodiments, the methazolamide particles have the following size distribution: a D(v, 0.1) of about 1 µm to 100 µm, a D(v, 0.5) of about 100 µm to 200 µm, and a D(v, 0.9) of about 200 µm to 300 µm. In some embodiments, the methazolamide particles have the following size distribution: a D(v, 0.1) of about 30 µm to 60 µm, a D(v, 0.5) of about 100 µm to 150 µm, and a D(v, 0.9) of about 240 µm to 290 µm. In some embodiments, the methazolamide particles have the following size distribution: a D(v, 0.1) of about 35 µm to 55 µm, a D(v, 0.5) of about 115 µm to 140 µm, and a D(v, 0.9) of about 250 µm to 275 µm.

The following conventions apply when describing particle size distribution. D(v, 0.1) means that 10% of the particles are smaller than this diameter. D(v, 0.5) is the median particle diameter. D(v, 0.9) means that 90% of the particles are smaller than this diameter.

The pharmaceutical compositions described herein can comprise a high molecular weight binder, which can control the release of methazolamide from the pharmaceutical composition. Low molecular weight binders have lower viscosities which result in faster drug release from the tablet and quicker drug release profiles. Suitable high molecular weight binders include, but are not limited to, hydroxypropyl methylcellulose, ethylcellulose, methylcellulose, sodium carboxymethylcellulose, hydroxypropyl cellulose, microcrystalline cellulose, starch, polyvinylpyrrolidone, sodium alginate, xantham gum and polyethylene glycols.

In a preferred embodiment, the high molecular weight binder is hydroxypropyl methylcellulose (HPMC) having a number average weight equal to or greater than about 80,000 daltons, and more preferably 100,000 daltons. Preferably, the hydroxypropyl methylcellulose has a methoxyl content of about 19-24%, a hydroxypropyl content of about 7-12%, and an apparent viscosity of about 80,000-120,000 cps in a 2% solution of water at about 20° C. In one embodiment, the HPMC is METHOCEL™ K 100M Premium CR (available from Dow Chemical Company). METHOCEL™ K 100M Premium CR is a hydroxypropyl methylcellulose which has a methoxyl content of about 19-24%, a hydroxypropyl content of about 7-12%, and an apparent viscosity of about 100,000 cps in a 2% solution of water at about 20° C.

In some embodiments, fillers can be added as a diluent to achieve the appropriate total tablet weight and hardness. Fillers useful in the present disclosure include, but are not limited to, lactose, microcrystalline cellulose, dextrose, calcium phosphate, calcium sulfate, sucrose, mannitol, and starch. In one preferred embodiment, the pharmaceutical compositions include the filler lactose.

In some embodiments, lubricants can be added to reduce friction, prevent tablet binding, and aid in the flow of mixture during the tableting process. Lubricants useful in the present disclosure include, but are not limited to, magnesium stearate, calcium stearate, zinc stearate, polyethylene glycol, sodium benzoate, sodium acetate, stearic acid, talc, hydrogenated vegetable oils, and starch. In one preferred embodiment, the pharmaceutical compositions include the lubricant magnesium stearate.

In some embodiments, flow agents can be added to maximize the efficiency of the manufacturing process by facilitating the flow of the particles through the tablet-forming equipment. Flow agents useful in the present disclosure include, but are not limited to, lactose, talc, silicon dioxide, polyethylene glycol, microcrystalline cellulose, sodium phosphate and calcium phosphate.

In some embodiments, the pharmaceutical compositions described herein comprise from about 10 to about 80 percent by weight methazolamide; from about 1 to about 60 percent by weight high molecular weight binder; from about 0 to about 5 percent by weight of lubricant; and from about 10 to about 90 percent by weight filler and/or flow agent. More preferably, the pharmaceutical compositions contain from about 30 to about 50 percent by weight methazolamide, from about 10 to about 20 percent by weight high molecular weight binder, from about 0 to about 2 percent by weight lubricant, and from about 28 to about 60 percent by weight fillers and/or flow agents. In one particular embodiment, the pharmaceutical composition comprises about 40 percent by weight methazolamide; about 15 percent by weight hydroxypropyl methylcellulose; from about 0 to about 2 percent by weight magnesium stearate; and from about 43 to about 45 percent by weight lactose.

These are preferred dose formulations giving desirable drug release profiles. These formulations provide a controlled release of methazolamide for about a twenty-four hour period. However, other formulations have been envisioned, which will also provide a controlled release of methazolamide over an extended period of time.

In some embodiments, the pharmaceutical compositions described herein have an in vitro drug release profile such that about 50% to about 80% of the methazolamide has been released at 12 hours and about 90-100% of the methazolamide has been released at 24 hours. In some embodiments, the pharmaceutical compositions described herein have an in vitro drug release profile such that no more than about 15%, about 20%, about 25%, or about 30% of the methazolamide has been released at 1 hour. In some embodiments, the pharmaceutical compositions described herein have an in vitro drug release profile such that no more than about 25%, about 30%, about 35%, about 40%, or about 45% of the methazolamide has been released at 3 hours. In some embodiments, the pharmaceutical compositions described herein have an in vitro drug release profile such that no more than about 40%, about 45%, about 50%, about 55%, or about 60% of the methazolamide has been released at 6 hours. In some embodiments, the pharmaceutical compositions described herein have an in vitro drug release profile such that no more than about 70%, about 75%, or about 80% of the methazolamide has been released at 12 hours. In some embodiments, the pharmaceutical compositions described herein have an in vitro drug release profile such that no more than about 90%, or about 95% of the methazolamide has been released at 18 hours. In some embodiments, the pharmaceutical compositions described herein have an in vitro drug release profile such that no less than about 80%, about 85%, about 90%, or about 95% of the methazolamide has been released at 24 hours.

In some embodiments, the pharmaceutical compositions described herein have an in vitro drug release profile such that no less than about 5%, about 10%, or about 15% of the methazolamide has been released at 1 hour. In some embodiments, the pharmaceutical compositions described herein have an in vitro drug release profile such that no less than about 10%, about 15%, about 20%, or about 25% of the methazolamide has been released at 3 hours. In some embodiments, the pharmaceutical compositions described herein have an in vitro drug release profile such that no less than about 20%, about 25%, about 30%, about 35%, or about 40% of the methazolamide has been released at 6 hours. In some embodiments, the pharmaceutical compositions described herein have an in vitro drug release profile such that no less than about 45%, about 50%, about 55%, about 60%, about 65%, about 70%, or about 75% of the methazolamide has been released at 12 hours. In some embodiments, the pharmaceutical compositions described herein have an in vitro drug release profile such that no less than about 70%, about 75%, about 80%, about 85%, or about 90% of the methazolamide has been released at 18 hours. In some embodiments, the pharmaceutical compositions described herein have an in vitro drug release profile such that about 90% to about 100% of the methazolamide has been released at 24 hours.

Drug release profiles can be determined using the testing procedures set forth below in the example embodiments section. The drug release profiles of the presently disclosed compositions help ensure that the methazolamide will be delivered in a sustained release manner such that a person need only take a single dose once per day in order to relieve intraocular pressure.

Methods of Manufacture

The pharmaceutical compositions of the present disclosure can be manufactured using any suitable means known to those of ordinary skill in the art. In one example, a sustained release methazolamide pharmaceutical composition is made by first mixing the pre-weighed dry ingredients (e.g. methazolamide, high molecular weight binder, fillers, etc.) in a blender and granulating the mixture with purified water using a high sheer mixer. The wet granules are dried in a fluid bed. Lubricant, if present in the pharmaceutical composition, can be part of the pre-weighed dry ingredients that are initially mixed, or it can be added to the fluid bed. Dried granules are then screened through a #16 mesh screen (1.19 mm), and only the retained granules are milled using a Fitzmill fitted with a #1B mesh screen at medium speed and knives forward. The milled composition is then finally blended using a double cone tumbler/blender and compressed into tablets. The size of the tablets is dependent on the amount of methazolamide in the tablet and the amount of other compounds used. Preferably, the tablets are between 100 and 800 mg each.

The pharmaceutical compositions can be made using other modifications to the process including, but not limited to, using a wet granulation fluid other than purified water, such as methanol, ethanol, isopropyl alcohol, or methylene chloride.

Methods of Treatment

Methods for treating an ocular condition characterized by elevated intraocular pressure are provided. In some embodiments, the methods for treating an ocular condition characterized by elevated intraocular pressure comprise administering once-daily to a subject in need thereof an extended release oral dose formulation of methazolamide as described herein. In some embodiments, a therapeutically effective amount of methazolamide is administered to a subject in need thereof in a therapeutically effective dosing regimen. A therapeutically effective amount of methazolamide, and its therapeutically effective dosing regimen, will be appreciated by those of ordinary skill in the art.

As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition. A therapeutically effective amount further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions.

In embodiments, methazolamide is administered to treat ocular conditions where lowering intraocular pressure is likely to be of therapeutic benefit, such as chronic open-angle glaucoma, secondary glaucoma, and preoperatively in acute angle-closure glaucoma where lowering the intraocular pressure is desired before surgery. In embodiments, methazolamide is administered preoperatively, postoperatively, or both, to lower intraocular pressure in a patient. In embodiments, the methods for treating an ocular condition characterized by elevated intraocular pressure comprise administering a therapeutically effective extended release oral dose formulation of methazolamide to a patient once-daily for 1, 2, 3, 4, 5, 6, 7, 8, 9, 10, 15, 20, 25, 30, or more days, as needed for intraocular pressure relief. In embodiments, the methazolamide, when administered in accordance with a therapeutically effective dosing regimen, contributes to lowering intraocular pressure in a subject without being toxic (e.g., without significant side effects) to the subject.

A dose of methazolamide can be administered alone or in combination with other medical treatments, or other therapeutic agents. When so used, other therapeutic agents can be administered before, concurrently (whether in separate dosage forms or in a combined dosage form), or after administration of methazolamide.

Example Embodiments

I. Formulations

In one exemplary embodiment, a pharmaceutical composition for treating an ocular condition is provided. The pharmaceutical composition is a controlled release tablet containing 100 or 150 mg of methazolamide and has the following formulation.

| Ingredient | % (by weight) | mg/Tablet | mg/Tablet |
|---|---|---|---|
| Methazolamide | 43.48 | 100 | 150 |
| HPMC (METHOCEL ™ K 100M Premium CR) | 15.07 | 34.67 | 52 |
| Lactose | 40.93 | 94.13 | 141.2 |
| Magnesium Stearate | 0.52 | 1.2 | 1.8 |
| Total | 100 | 230 | 345 |

These are preferred dose formulations giving desirable drug release profiles. These formulations provide an approximately consistent release of methazolamide for about a twenty-four hour period. However, other formulations have been envisioned, which will also provide an approximately consistent release of methazolamide over an extended period of time.

The tablets having the above exemplary formulation can be manufactured by a wet granulation method. In one example, all ingredients are weighed based on either the 100 or 150 mg methazolamide formulation. The methazolamide, HPMC (METHOCEL™ K 100M Premium CR), and lactose are mixed in a blender. The mixed composition is granulated with purified water using a high sheer mixer. The wet granules are dried in a fluid bed, and the lubricant magnesium stearate is added to the fluid bed. The dried granules are then screened through a #16 mesh screen (1.19 mm), and only the retained granules are milled using a Fitzmill fitted with a #1B mesh screen at medium speed and knives forward. The milled composition is then finally blended using a double cone tumbler/blender and compressed into tablets.

II. Testing

Methazolamide particle size testing was performed on unmilled methazolamide particles and methazolamide particles milled in-house and by a third party vendor according to the above milling procedure. Methazolamide particle size testing was conducted using a Mastersizer laser particle size analyzer from Malvern Instruments or a sonic shifter. The results of the particle size testing for methazolamide particles milled in-house, as measured by a laser particle size analyzer, are as follows:

| Sample | D(v, 0.1) | D(v, 0.5) | D(v, 0.9) |
|---|---|---|---|
| 1 | 42.15 μm | 121.45 μm | 255.75 μm |
| 2 | 47.67 μm | 132.34 μm | 269.30 μm |
| 3 | 48.42 μm | 128.46 μm | 267.26 μm |
| Average | 46.1 μm | 127.4 μm | 264.1 μm |

The results of the particle size testing for unmilled methazolamide particles, methazolamide particles milled in-house, and methazolamide particles milled by a third party vendor, as measured by a sonic shifter, are as follows:

| | % Retained | | |
|---|---|---|---|
| Sieve # | Unmilled API | Milled API (in-house) | Milled API ($3^{rd}$ party) |
| 20 (840 μm) | 0.09 | 1.23 | 5.15 |
| 40 (420 μm) | 7.95 | 1.52 | 6.14 |
| 80 (177 μm) | 75.05 | 15.27 | 21.88 |
| 100 (149 μm) | 8.04 | 19.54 | 17.14 |
| 140 (105 μm) | 6.01 | 32.92 | 21.90 |
| 200 (74 μm) | 2.03 | 13.00 | 12.29 |
| Fines Collector | 0.83 | 16.51 | 15.56 |
| Density | | | |
| Bulk Density | 0.92 g/mL | 0.56 g/mL | 0.53 g/mL |
| Trapped Density | 1.03 g/mL | 0.99 g/mL | 1.00 g/mL |

Drug release testing was performed on the exemplary formulations described above to determine the specific drug release profiles. The method was based upon the current U.S. Pharmacopeia (USP) XXIII (The United States Pharmacopeial Convention, Inc., Rockville, Md., 1998) dissolution test procedure for immediate release products. The method included using a USP Paddle Apparatus II at 100 rpm with acetate buffer (pH=4.5) medium with various sampling points. In the method, a tablet was dropped into the apparatus and the amount of methazolamide dissolved in the acetate buffer solution was measured over various time periods as measured by UV spectrophotometry at λ=280 nm using a HPLC equipped with a UV detector, as is well known in the art. This method gave the following dissolution profiles (e.g. drug release profiles) of the tablets containing 100 mg or 150 mg of methazolamide:

| Ingredient | 1 hr | 3 hrs | 6 hrs | 12 hrs | 18 hrs | 24 hrs |
|---|---|---|---|---|---|---|
| 100 mg tablet | | | | | | |
| % released | 12 | 22 | 38 | 68 | 87 | 98 |
| mg equiv. | 12 | 22 | 38 | 68 | 87 | 98 |
| 150 mg tablet | | | | | | |
| % released | 12 | 21 | 35 | 61 | 82 | 93 |
| mg equiv. | 18 | 31.5 | 52.5 | 91.5 | 123 | 139.5 |

The drug release profile showed a release of about 60-80% methazolamide at 12 hours and a >90% release of methazolamide at 24 hours.

The detailed description set forth above is provided to aid those skilled in the art in practicing the invention. However, the invention described and claimed herein is not to be limited in scope by the specific embodiments described above, as these embodiments are presented as mere illustrations of several aspects of the invention. Any combinations and modifications of the described methods and components, and compositions used in the practice of the methods, in addition to those not specifically described, will become apparent to those skilled in the art based on the present disclosure and do not depart from the spirit or scope of the present invention. Such variations, modifications, and combinations are also encompassed by the present disclosure and fall within the scope of the appended claims.

What is claimed is:

1. A once-a-day controlled release oral dosage form comprising:
   100 mg to 200 mg of a drug selected from methazolamide, a pharmaceutically acceptable salt of methazolamide, or a combination thereof; and
   a high molecular weight binder;
   wherein the dosage form provides an in vitro release of from about 50% to about 80% by weight of the drug at 12 hours when measured by the USP Paddle Method at 100 rpm in acetate buffer (pH=4.5),
   wherein the dosage form provides an in vitro release of about 90% or greater by weight of the drug at 24 hours when measured by the USP Paddle Method at 100 rpm in acetate buffer (pH=4.5), and
   wherein the dosage form is configured to release the drug in vivo over_an entire 24 hour period.

2. The controlled release oral dosage form of claim 1, wherein the controlled release oral dosage form is a tablet.

3. The controlled release dosage form of claim 1, wherein the drug is methazolamide.

4. The controlled release dosage form of claim 1, wherein the controlled release oral dosage form comprises about 125 mg of the drug.

5. The controlled release dosage form of claim 1, wherein the controlled release oral dosage form comprises about 175 mg of the drug.

6. The controlled release oral dosage form of claim 1, wherein the controlled release oral dosage form comprises about 150 mg of the drug.

7. The controlled release oral dosage form of claim 1, wherein the high molecular weight binder is hydroxypropyl methylcellulose (HPMC).

8. The controlled release oral dosage form of claim 7, wherein the HPMC has a methoxyl content of about 19-24% and a hydroxypropyl content of about 7-12%.

9. The controlled release oral dosage form of claim 1, wherein the high molecular weight binder has an apparent viscosity of about 80,000-120,000 cps in a 2% solution of water at about 20° C.

10. The controlled release oral dosage form of claim 1, wherein the high molecular weight binder has a number average weight equal to or greater than about 80,000 daltons.

11. The controlled release oral dosage form of claim 1, wherein the high molecular weight binder is HPMC, wherein the HPMC has a methoxyl content of about 19-24% and a hydroxypropyl content of about 7-12%, wherein the HPMC has a number average weight equal to or greater than about 80,000 daltons, and wherein the HPMC has an apparent viscosity of about 80,000-120,000 cps in a 2% solution of water at about 20° C.

12. The controlled release oral dosage form of claim 1, further comprising a filler, a lubricant, a flow agent, or a combination thereof.

13. The controlled release oral dosage form of claim 1, further comprising a filler and a lubricant.

14. The controlled release oral dosage form of claim 13, wherein the filler is lactose, and wherein the lubricant is magnesium stearate.

15. The controlled release oral dosage form of claim 12, wherein the controlled release oral dosage form comprises about 40% by weight of the drug, about 15% by weight of the high molecular weight binder, about 44.5% by weight of the filler, and about 0.5% by weight of the lubricant.

16. The controlled release oral dosage form of claim 1, wherein the drug has a particle size distribution as follows: a D(v, 0.1) of about 1 μm to 100 μm, a D(v, 0.5) of about 100 μm to 150 μm, and a D(v, 0.9) of about 200 μm to 300 μm.

17. The controlled release oral dosage form of claim 1, wherein the dosage form provides an in vitro release such that 20% to 40% by weight of the drug is released at 6 hours when measured by the USP Paddle Method at 100 rpm in acetate buffer (pH=4.5).

18. The controlled release oral dosage form of claim 1, wherein the dosage form provides an in vitro release of from about 60% to about 70% by weight of the drug at 12 hours when measured by the USP Paddle Method at 100 rpm in acetate buffer (pH=4.5).

19. A method for treating an ocular condition characterized by elevated intraocular pressure comprising:
   administering to a patient in need thereof a controlled release oral dosage form according to claim 1.

20. A once-a-day controlled release oral dosage form comprising:
   methazolamide or a pharmaceutically acceptable salt thereof;
   a high molecular weight binder;
   a filler; and
   a lubricant;
   wherein the dosage form provides an in vitro release of from about 50% to about 80% by weight of the drug at 12 hours when measured by the USP Paddle Method at 100 rpm in acetate buffer (pH-4.5),
   wherein the dosage form provides an in vitro release of about 90% or greater by weight of the drug at 24 hours when measured by the USP Paddle Method at 100 rpm in acetate buffer (pH=4.5), and
   wherein the methazolamide or pharmaceutically acceptable salt thereof has a particle size distribution as follows: a D(v, 0.1) of about 1 μm to 100 μm, a D(v, 0.5) of about 100 μm to 150 μm, and a D(v, 0.9) of about 200 μm to 300 μm.

* * * * *